US010245237B2

(12) United States Patent
De Vries et al.

(10) Patent No.: US 10,245,237 B2
(45) Date of Patent: *Apr. 2, 2019

(54) COMPRESSED TABLET CONTAINING CANNABIDIOL, METHOD FOR ITS MANUFACTURE AND USE OF SUCH TABLET IN ORAL TREATMENT OF PSYCHOSIS OR ANXIETY DISORDERS

(71) Applicant: Echo Pharmaceuticals B.V., Weesp (NL)

(72) Inventors: Jan Albert De Vries, Zelhem (NL); Maria Vanesa Fernandez Cid, Haarlem (NL); Ana Maria Heredia Lopez, Amsterdam (NL); Cristina Maria Eiroa Martinez, Amsterdam (NL)

(73) Assignee: Echo Pharmaceuticals B.V., Weesp (NL)

(*) Notice: Subject to any disclaimer, the term of this patent is extended or adjusted under 35 U.S.C. 154(b) by 0 days.

This patent is subject to a terminal disclaimer.

(21) Appl. No.: 15/874,544

(22) Filed: Jan. 18, 2018

(65) Prior Publication Data

US 2018/0140560 A1    May 24, 2018

Related U.S. Application Data

(63) Continuation of application No. 15/032,905, filed as application No. PCT/NL2014/050745 on Oct. 29, 2014, now Pat. No. 9,943,491.

(30) Foreign Application Priority Data

Oct. 29, 2013  (EP) ..................... 13190587

(51) Int. Cl.
*A61K 31/05* (2006.01)
*A61K 9/20* (2006.01)

(52) U.S. Cl.
CPC ............ *A61K 31/05* (2013.01); *A61K 9/2018* (2013.01); *A61K 9/2072* (2013.01); *A61K 9/2095* (2013.01)

(58) Field of Classification Search
None
See application file for complete search history.

(56) References Cited

U.S. PATENT DOCUMENTS

| 2002/0015730 A1 | 2/2002 | Hoffman |
| 2003/0021752 A1 | 1/2003 | Whittle |
| 2006/0076536 A1 | 4/2006 | Barshied |
| 2010/0008985 A1 | 1/2010 | Pellikaan et al. |
| 2010/0034888 A1 | 2/2010 | Pellikaan et al. |
| 2011/0038958 A1 | 2/2011 | Kikuchi et al. |

FOREIGN PATENT DOCUMENTS

| WO | WO-02/064109 A2 | 8/2002 |
| WO | WO-2006/063109 A2 | 6/2006 |
| WO | WO-2006/133941 A2 | 12/2006 |
| WO | WO-2008/024490 A2 | 2/2008 |
| WO | WO-2008/033023 A2 | 3/2008 |
| WO | WO-2008/033024 A2 | 3/2008 |
| WO | WO-2009/020666 A2 | 2/2009 |
| WO | WO-2009/087351 A1 | 7/2009 |
| WO | WO-2012/033478 A1 | 3/2012 |

OTHER PUBLICATIONS

Leweke, F.M.; Piomelli, D.; Pahlisch, F.; Muhl, D.; Gerth, C.W>; Hoyer, C.; Klosterkotter, J.; Hellmich, M.; Koethe, D. Cannabidiol enhances anandamide signaling and alleviates psycotic symptoms of shizophrenia. Transl. Psychiatry, 2012, pp. 1-7.*
Crippa, J. A. S.; Derenusson, G. N.; Ferrari, T. B.; Wichert-Ana, L. Duran, F. L.S.; Martin-Santos, R.; Simoes, M.V.; Bhattacharyya, S.et al. Neural basis of anxiolytic effects of cannabidiol (CBD) in generalized social anxiety disorder: a preliminary report. J. Pyschopharm, 2011, 25(1) pp. 121-130.*
International Search Report issued in International Patent Application No. PCT/NL2014/050745 dated Feb. 4, 2015.
International Search Report issued in International Patent Application No. PCT/NL2014/050746 dated Jan. 19, 2015.
Leweke et al., "Cannabidiol enhances anandamide signaling and alleviates psychotic symptoms of schizophrenia", Translational Psychiatry, 2012, vol. 2, pp. 1-7.
Munjal et al. "Polymeric Systems for Amorphous delta9-Tetrahydrocannabinol Produced by a Hot-Melt Method. Part II: Effect of Oxidation Mechanisms and Chemical Interactions on Stability", J Pharm Sci. Nov. 2006, vol. 95, No. 11, pp. 2473-2485.
Ohlsson et al., "Plasma delta-9-tetrahydrocannabinol concentrations and clinical effects after oral and intravenous administration and smoking",Clin. Pharmacol. Ther., Sep. 1980, vol. 28, pp. 409-416.
Ohlsson et al., "Single dose kinetics of deuterium labelled delta-1-tetrahydrocannabinol in heavy and light cannabis users" Biomedical Mass Spectrometry, 1982, vol. 9, No. 1, pp. 6-10.

(Continued)

*Primary Examiner* — Jessica Worsham
(74) *Attorney, Agent, or Firm* — Gilberto M. Villacorta; Sunit Talapatra; Foley & Lardner LLP

(57) ABSTRACT

The present invention relates to compressed tablets for peroral delivery of the cannabinoid cannabidiol (CBD). More particularly, the invention provides a compressed tablet having a tablet weight of 60-1200 mg, said tablet being composed of:
  50-95 wt. % of a granulate;
  5-50 wt. % of lactose; and
  0-30 wt. % of other tablet excipients;
wherein the granulate contains:
a. 2-15 wt. % of cannabidiol;
b. 2-30 wt. % of sucrose fatty acid mono-ester;
c. 30-96 wt. % of lactose; and
d. 0-25 wt. % of other granulate excipients.
The compressed tablets according to the invention can conveniently be used in the treatment of psychosis disorders or anxiety disorders.
The invention further provides a method for the manufacture of the compressed tablets.

14 Claims, No Drawings

(56) References Cited

OTHER PUBLICATIONS

Poortman-Van Der Meer et al., "A contribution to the improvement of accuracy in the quantitation of THC", Forensic Science International, 1999, vol. 101, pp. 1-8.
Zhornitsky et al., "Cannabidiol in humans—the quest for therapeutic targets", Pharmaceuticals, 2012, vol. 5, pp. 529-552.
Zuardi et al., "Cannabidiol monotherapy for treatment-resistant schizophrenia", Journal of Psychopharmacology, 2006, vol. 20, No. 5, pp. 683-686.
Zuardi et al., "Cannabidiol, a Cannabis sativa constituent, as an antipsychotic drug", Brazilian Journal of Medical and Biological Research, 2006, vol. 39, pp. 421-429.

* cited by examiner

COMPRESSED TABLET CONTAINING CANNABIDIOL, METHOD FOR ITS MANUFACTURE AND USE OF SUCH TABLET IN ORAL TREATMENT OF PSYCHOSIS OR ANXIETY DISORDERS

CROSS-REFERENCE TO RELATED APPLICATIONS

This application is a Continuation of U.S. patent application Ser. No. 15/032,905, filed Apr. 28, 2016, which is the U.S. National Phase of International Patent Application No. PCT/NL2014/050745, filed Oct. 29, 2014, published on May 7, 2015 as WO 2015/065179 A1, which claims priority to European Patent Application No. 13190587.9, filed Oct. 29, 2013. The contents of these applications are herein incorporated by reference in their entirety.

TECHNICAL FIELD OF THE INVENTION

The present invention relates to compressed tablets containing a granulate comprising lactose particles, cannabidiol and a sucrose fatty acid mono-ester. These compressed tablets are particularly suited for peroral administration and can be conveniently used in peroral treatment of psychosis or anxiety disorders. The invention also provides a method for the manufacture of the compressed tablets.

BACKGROUND OF THE INVENTION

The use of antipsychotic drugs for the treatment of schizophrenia-like symptoms is often associated with adverse side effects such as motor disturbances, weight gain and sexual dysfunction. Hence, there is a continuous need for alternative well-tolerated antipsychotic drugs.

It has been known since long that different components of the plant Cannabis sativa (cannabis) have pharmacological activity. Cannabis contains various cannabinoids, two of which have almost opposing actions. Δ9-Tetrahydrocannabinol (THC), which is the most abundant cannabinoid in smoked cannabis, is known to be a psychotomimetic component. In contrast, cannabidiol (CBD), which is another major cannabinoid found in some strains of cannabis, has been found to have antipsychotic properties.

The antipsychotic properties of CBD have been investigated. Publications describing studies in which schizophrenic patients were treated with CBD indicate that CBD is a well-tolerated alternative drug for the treatment of for example schizophrenia.

CBD is a lipophilic substance that is not soluble in water. It is soluble in ethanol (36 mg/ml) and dimethylsulfoxide DMSO (60 mg/ml). CBD has a melting point of about 66° C.

Bioavailability of pharmaceutical substances taken perorally, first of all, depends on the extent to which the pharmaceutically active substance is absorbed from the intestinal environment across the intestinal mucosa. Lipophilic pharmaceutical substances are generally poorly absorbed from the intestinal environment, inter alia because of their poor solubility and/or dispersibility in water.

Bioavailability of a pharmaceutical substance taken perorally furthermore depends on the susceptibility of the substance to the so-called first pass effect. Substances absorbed from the intestine, before being distributed throughout the body, have to pass the liver first where they may be metabolized immediately. CBD is generally assumed to be rather susceptible to first-pass liver metabolization.

Oral bioavailability of CBD is low and unpredictable (S. Zhornitsky, S. Potvin, Pharmaceuticals (2012) 5, 529-552). In addition, CBD is an unstable drug (A. J. Poortman, H. Huizer, *Forensic Science International* (1999) 101, 1-8).

Therapeutic applications of CBD have been described in several publications.

F. M. Leweke et al. (*Transl. Psychiatry* (2012) 2, e94) describe the treatment of humans of age between 18 and 50 years old suffering from acute paranoid schizophrenia by daily administering 200 to 800 mg CBD or a similar dose of the potent antipsychotic drug amisulpride.

A. W. Zuardi et al. (*Braz. J. Med. Biol. Res.* (2006) 39, 421-429 and *Journal of Psychopharmacology* (2006) 20(5), 683-686) describe a case study in which a schizophrenic patient received high doses of CBD (dissolved in oil) up to 1500 mg/day for 4 weeks and showed significant improvement during CBD treatment while a worsening was observed when the administration was interrupted. In another case study, a patient with a diagnosis of schizophrenia was administered doses of CBD, starting with 40 mg/day for 5 days, with the dose being doubled every 5 days up to 1280 mg/day during a period of about 4 weeks. A trend for symptom improvement was observed at a dose of 1280 mg/day.

US 2011/038958 relates to a method for treatment or prevention of psychosis or a psychotic disorder. The method of treatment comprises administering to a patient a therapeutically effective amount of tetrahydrocannabivarin (THCV) and/or CBD. US 2011/038958 describes an experiment in which mice received once daily oral doses of 0.3 and 3 mg/kg CBD in combination with pure THCV.

WO 2008/033024 describes dosage units for sublingual, buccal or oral administration of water-insoluble pharmaceutically active substances. CBD is mentioned as an example of water-insoluble pharmaceutically active substances. Example 1 describes the preparation of a monophasic microgranulate comprising the cannabinoid Δ-9-tetrahydrocannabinol, and sucrose monolaurate in a weight ratio of 1:15 using a dry granulation process. Example 3 of this patent application describes the manufacture of a tabletting powder for direct compression using 5 g of the microgranulate obtained from Example 1 and 17 g of other components including 5 g of lactose and the compression to 7 mm tablets with a total weight of 60 mg. Example 6 describes the preparation of tablets containing 61 mg of a microgranulate, 180 mg lactose and 10 mg of other excipients, said microgranulate being composed of Δ-9-tetrahydrocannabinol (THC), sucrose monolaurate and xylitol. The microgranulate was prepared by successively dispersing sucrose monolaurate and xylitol into molten xylitol, followed by cooling and grinding.

WO 02/064109 describes a pharmaceutical formulation for use in administration of a lipophilic medicament via a mucosal surface, which formulation comprises at least one lipophilic medicament and at least one self emulsifying agent. Also described are pharmaceutical formulations in the form of a gel or a compressed tablet for administration of a lipophilic medicament via the sublingual and/or buccal mucosa. Among the lipophilic medicaments mentioned in WO 02/064109 A2 are THC and mixtures of THC and CBD. The pharmaceutical formulations are intended for the treatment of a variety of diseases among which are multiple sclerosis, spinal cord injury, peripheral neuropathy and other neurogenic pain. Example 6 of the patent application describes the preparation of a tablet for buccal or sublingual administration by dissolving glyceryl monostearate, polysorbate 80, ascorbyl palmitate and α-tocopherol and THC in alcohol, spraying the alcoholic solution onto a powder mix consisting of lactose and soluble starch, evaporating the alcohol, dusting the resulting granulate with talc and compressing to a target tablet weight of 101 mg.

WO 2009/087351 describes the use of one or more phyto-cannabinoids, including CBD, with one or more antipsychotic medications in the manufacture of a pharmaceutical formulation for use in the prevention or treatment of psychosis or a psychotic disorder, wherein the one or more phyto-cannabinoids are administered separately, sequentially or simultaneously to the one or more anti-psychotic medicaments.

WO 2012/033478 describes an oral dosage form of cannabinoids, among which CBD, in a self-emulsifying system operable to avoid hepatic first pass metabolism, said oral dosage form comprising:
- 1-90 wt. % of a pharmacologically active form of cannabinoids;
- 15-85 wt. % of one or more triglycerides;
- 15-85 wt. % of one or more mixed glycerides; and
- 5-90 wt. % of a surfactant which promotes self-emulsification.

It is an object of the present invention to provide a dosage unit for peroral administration of CBD that combines high and predictable bioavailability with excellent stability. It is a further object of the invention to provide dosage units for peroral administration of CBD that can conveniently be used in the treatment of psychosis disorders or anxiety disorders.

SUMMARY OF THE INVENTION

The inventors have developed a compressed tablet for peroral delivery that meets these objectives. The tablet according to the present invention has a tablet weight of 60-1200 mg and is composed of: 50-95 wt. % of a CBD-containing granulate, 5-50 wt. % of lactose and 0-30 wt. % of other tablet excipients. The granulate contains 2-15 wt. % of CBD, 2-30 wt. % of sucrose fatty acid mono-ester, 30-96 wt. % of lactose and 0-25 wt. % of other granulate excipients.

The oral bioavailability of the CBD in the tablets of the present invention is high as well as predictable. Furthermore, the compressed tablets are very stable in that CBD degradation during storage under ambient conditions is minimal. The tablets according to the invention can conveniently be used in the treatment of psychosis disorders or anxiety disorders at daily doses in a total amount that is equivalent to 5-1000 mg of CBD.

The invention further relates to a method of manufacturing a compressed tablet according to the present invention, said method comprising the steps of:
- providing a lactose powder having a mass weighted average diameter of 32-250 µm;
- combining the lactose powder with a granulation fluid to produce a granulate, said granulation fluid comprising a solution of CBD, sucrose fatty acid monoester, antioxidant and optionally further granulate excipients in organic solvent;
- removing the organic solvent by evaporation to produce a granulate;
- mixing the granulate with lactose and optionally further tablet excipients to produce a tablet mixture; and
- compressing the tablet mixture into a tablet.

Definitions

The term 'compressed tablet' as used herein refers to a mixture of active substances and excipients, pressed or compacted from a powder form into the solid pharmaceutical dosage form.

The term 'granulate' as used herein refers to a particulate material that consists of discrete particles, referred to as granules.

The term 'granule' refers to a particle that is composed of two or more sub-particles that are held together by physical forces, e.g. by a binding agent.

The term 'granulation' as used herein refers to a process that converts a powder into a granulate. Wet granulation is a granulation method that employs a liquid to convert a powder into a granulate. The fluid is usually sprayed onto the powder while the powder is kept in motion. The fluid acts as a binding agent that 'glues' together the powder particles, thereby forming granules. This fluid is also referred to herein as 'granulation fluid'. It typically contains a solvent which is sufficiently volatile for removal by drying and that is non-toxic.

The term 'oral' or 'peroral' as used herein, unless indicated otherwise, refers to a mode of administration that involves ingestion of the dosage unit.

The term 'mass weighted average diameter' as used herein refers to the average diameter of particulate matter wherein the contribution of the diameter of a single particle to the average is proportional to the mass of that single particle. The mass weighted average diameter of a powder or a granulate may suitably be measured by analytical sieve analysis.

The term 'volume weighted average diameter' as used herein refers an average particle diameter wherein the contribution of the diameter of a single particle to the average is proportional to the volume of that single particle. The relative volume-contribution of a single particle is usually assumed to be proportional to its $(diameter)^3$.

The term 'solid dispersion' refers to compositions containing a drug dispersed or dissolved within a solid carrier matrix. Different types of solid dispersions can be distinguished on the basis of the physical form of the drug and the carrier. The drug is either suspended in the carrier as phase-separated crystalline or amorphous particles, or it exists as a homogeneous molecular mixture of (amorphous) drug and carrier. The carrier can exist in amorphous or crystalline form. More information on solid dispersions can be found in Williams et al., Strategies to Address Low Drug Solubility in Discovery and Development, *Pharmacological Reviews* (2013) 65, 416-445.

The term 'psychosis disorders' as used herein refers to a disorder that is accompanied by psychosis or psychotic symptoms.

The term 'psychosis' as used herein refers to a mental illness typically characterized by radical changes in personality, impaired functioning, and a distorted or nonexistent sense of objective reality. Patients suffering from psychosis have impaired reality testing; that is, they are unable to distinguish personal subjective experience from the reality of the external world. They experience hallucinations and/or delusions that they believe are real, and may behave and communicate in an inappropriate and incoherent fashion. Psychosis may appear as a symptom of a number of mental disorders, including mood and personality disorders. It is also the defining feature of schizophrenia, schizophreniform disorder, schizoaffective disorder, delusional disorder, and the psychotic disorders (i.e., brief psychotic disorder, shared psychotic disorder, psychotic disorder due to a general medical condition, and substance-induced psychotic disorder).

The term 'anxiety disorders' as used herein refers to mental disorders in which anxiety and avoidance behavior predominate. Examples of such disorders include phobias (including agoraphobia), panic disorder, obsessive-compulsive disorder, posttraumatic stress disorder, acute stress disorder, generalized anxiety disorder, and substance-induced anxiety disorder.

DETAILED DESCRIPTION OF THE INVENTION

A first aspect of the invention relates to a compressed tablet having a tablet weight of 60-1200 mg, said tablet being composed of 50-95 wt. % of a granulate, 5-50 wt. % of lactose and 0-30 wt. % of other tablet excipients, wherein the granulate contains 2-15 wt. % of CBD, 2-30 wt. % of sucrose fatty acid mono-ester, 30-96 wt. % of lactose and 0-25 wt. % of other granulate excipients.

The compressed tablet of the present invention is composed of (prepared from) at least two particulate components, i.e. granulate, lactose and optionally one or more excipients. Unless indicated otherwise the lactose concentrations mentioned herein refer to either the lactose that together with the granulate represents the bulk of the compressed tablet or the lactose that is contained within the granulate.

The weight of the compressed tablet preferably is within the range of 100-1000 mg, more preferably in the range of 200-800 mg and most preferably in the range of 250-500 mg.

The amount of CBD contained in the compressed tablet preferably lies within the range of 2-100 mg, more preferably in the range of 5-90 mg and most preferably in the range of 10-80 mg.

The CBD-containing granulate typically represents at least 55 wt. %, more preferably at least 58 wt. % and most preferably at least 60 wt. % of the tablet. Preferably, said granulate represents not more than 90 wt. %, especially not more than 85 wt. % and most preferably not more than 80 wt. % of the tablet.

Lactose, other than the lactose contained in the CBD-containing granulate, typically represents of at least 10 wt. %, more preferably of at least 15 wt. % and most preferably of at least 20 wt. % of the tablet. Preferably, said lactose represents not more than 46 wt. %, more preferably not more than 43 wt. % and most preferably not more than 40 wt. % of the tablet.

The optional other tablet excipients are typically contained in the tablet in a concentration of not more than 25 wt. %, more preferably in a concentration of not more than 22 wt. % and most preferably in a concentration of not more than 20 wt. %.

CBD is preferably contained in the granulate in a concentration of at least 4 wt. %, especially of at least 5 wt. %.

Sucrose fatty acid mono-ester typically represent at least 5 wt. %, more preferably at least 8 wt/% and most preferably at least 10 wt. % of the granulate. Preferably the concentration of sucrose fatty acid mono-ester in the granulate does not exceed 27 wt. %, most preferably it does not exceed 25 wt. %.

Lactose is typically contained in the CBD-containing granulate in a concentration of at least 45 wt. %, more preferably of at least 55 wt. % and most preferably of at least 60 wt. %. The lactose content of the granulate preferably does not exceed 90 wt. %. More preferably, the lactose content of the granulate does not exceed 85 wt. %, even more preferably it does not exceed 80 wt. %. Most preferably, said lactose content does not exceed 78 wt. %.

The optional other granulate excipients are typically contained in the granulate in a concentration of not more than 22 wt. %, most preferably in a concentration of not more than 20 wt. %. The term 'granulate excipients' as used in the context of the present invention is not to be construed narrowly. Non-limiting examples of excipients that can conveniently be used in the granulate are preservatives, fats, waxes, and further pharmaceutically active substances, such as further cannabinoids or analgesic drugs.

In an embodiment of the invention, a compressed tablet is provided as defined herein, with the proviso that it is not a compressed tablet comprising 75 wt % of a granulate, 23.8 wt. % of lactose, 1 wt % of magnesium stearate and 0.2 wt % of silicon dioxide, wherein the granulate contains 8.0 wt. % of CBD, 16.0 wt. % of sucrose monolaurate, 75.2 wt. % of lactose and 0.8 wt. % of ascorbic acid.

In a preferred embodiment, the granulate is composed of granules, said granules comprising lactose particles that are held together by a solid dispersion containing the CBD, sucrose fatty acid mono-ester and optionally other granulate excipients.

The solid dispersion comprising CBD and sucrose fatty acid mono-ester is clearly distinguishable from the lactose particles and acts as a 'glue' that holds together the lactose particles within the granules that make up the granulate.

In an even more preferred embodiment, the granulate is composed of granules, said granules comprising lactose particles that are held together by a solid dispersion, wherein the solid dispersion contains a dispersed phase comprising CBD. Preferably, said dispersed phase comprising CBD has a volume weighted average diameter between 2 nm and 1 μm, more preferably of 2-500 nm, most preferably of 2-300 nm. The person skilled in the art is familiar with suitable techniques for determining the volume weighted average diameter of the dispersed phase containing CBD. Transmission electron microscopy is an example of a analytical technique that can be used to determine the volume weighted average diameter of the dispersed phase of the solid dispersion.

In a preferred embodiment, the granules constituting the granulate has a mass weighted average diameter of 50-1000 μm, more preferably of 90-500 μm and most preferably of 160-355 μm.

In a preferred embodiment the lactose constituting the lactose particles within the granulate is anhydrous lactose (β-lactose) or α-lactose monohydrate. Anhydrous lactose is substantially free of (crystal) water. α-lactose monohydrate is lactose in which the lactose molecule is associated with 1 molecule of water. The water is incorporated in the crystal lattice and forms an integral part of it. Most preferably, the lactose contained in the granules is α-lactose monohydrate.

In a preferred embodiment, 70-100 wt. % of the lactose within the granulate consists of α-lactose monohydrate, more preferably 75-100 wt. %, even more preferably 80-100 wt. %.

In a preferred embodiment, 90-100 wt. % of the lactose contained within the granulate consists of crystalline lactose, more preferably 95-100 wt. %, even more preferably 98-100 wt. %.

In a preferred embodiment, the lactose within the granulate is a spray-dried lactose. Preferably the lactose used for producing the granulate is obtainable by spray-drying a suspension of fine milled α-lactose monohydrate crystals in a solution of lactose. As is known by those of average skill, lactose produced via spray-drying is morphologically distinguishable from other lactose materials in that the particles are spherical or substantially spherical, which proved advantageous in the production of the granulate.

The CBD-containing granulate preferably contains 0.2-1.5 wt. %, more preferably 0.4-1.2 wt % of antioxidant. The inventors have found that the inclusion of antioxidant significantly improves the stability of the CBD within the tablet.

In a preferred embodiment of the invention, the ratio of antioxidant to CBD (w/w) is within the range of 1:40-1:3, more preferably of 1:20-1:5, and most preferably of 1:15-1:7.5.

Non-limiting examples of antioxidants that can be employed in the granulate include α-tocopherol (vitamin E), ascorbic acid (vitamin C), esters of ascorbic acid, vitamin A, flavanoids, polyphenols, butylated hydroxy anisole, carotenes, ubiquinol (coenzyme Q10), and combinations thereof. In a preferred embodiment the antioxidant is selected from ascorbic acid, esters of ascorbic acid and combinations thereof. Examples of esters of ascorbic acid that may be employed include fat-soluble esters of ascorbic acid with long-chain fatty acids (e.g. ascorbyl palmitate or ascorbyl stearate). Most preferably, the antioxidant employed is ascorbic acid.

As explained herein before THC is known to be a psychotomimetic component. This means that THC may produce effects that resemble or are identical with psychotic symptoms such as hallucinations or paranoid delusions. The presence of THC in the compressed tablets according to the invention can therefore counteract the intended antipsychotic properties of the CBD and its concentration in the compressed tablets according to the invention is therefore preferably kept low. Hence, in a preferred embodiment, the compressed tablet contains 0-5% THC by weight of CBD. In an even more preferred embodiment, the compressed tablet contains 0-2% THC by weight of CBD. In a most preferred embodiment, the compressed tablet contains less than 0.5% THC by weight of CBD.

Sucrose fatty acid mono-esters are amphiphilic compounds, i.e. they comprise a hydrophilic and a lipophilic part. The balance between their hydrophilicity and lipophilicity can be expressed in the so-called HLB value. According to a particularly preferred embodiment, the sucrose fatty acid mono-ester has an HLB-value of 8-18, more preferably of 11-17 and most preferably of 13-16.

In a preferred embodiment, the fatty acid residue of the sucrose fatty acid mono-ester, is selected from $C_8$-$C_{18}$ fatty acids. In an even more preferred embodiment, the fatty acid residue of the sucrose fatty acid mono-ester is a saturated $C_{10}$-$C_{18}$ fatty acid. In an even more preferred embodiment, the fatty acid residue of the sucrose fatty acid mono-ester is selected from lauric, palmitic or stearic acid. In a most preferred embodiment, the sucrose fatty acid mono-ester is sucrose mono-laurate.

In a preferred embodiment of the invention, the granulate contains 5-15 wt. % of CBD, 10-25 wt. % of sucrose fatty acid mono-ester, 60-78 wt. % of lactose and 0-8 wt. % of other granulate excipients.

In a preferred embodiment of the invention, the ratio of CBD to sucrose fatty acid mono-ester in the granulate is within the range of 1:4-1:1, more preferably 1:3-1:1.5.

In a preferred embodiment of the invention, the lactose that is combined with the granulate and optional other tablet excipients to form the compressed tablet, is anhydrous lactose (β-lactose) or α-lactose monohydrate, most preferably it is α-lactose monohydrate. In a preferred embodiment, 70-100 wt. % of the lactose within the granulate consists of α-lactose monohydrate, more preferably 75-100 wt. %, even more preferably 80-100 wt. %. In a preferred embodiment, 90-100 wt. % of the lactose consists of crystalline lactose, more preferably 95-100 wt. %, even more preferably 98-100 wt. %. In a preferred embodiment, the lactose within the granulate is a spray-dried lactose. Preferably the lactose used for producing the granulate is obtainable by spray-drying a suspension of fine milled α-lactose monohydrate crystals in a solution of lactose.

Commercially available sucrose fatty acid mono-esters usually contain small amounts of sucrose fatty acid di-esters. The present granulate preferably comprises less than 50 wt. % of sucrose fatty acid di-ester by weight of the sucrose fatty acid mono-ester, more preferably less than 10 wt. % of sucrose di-esters by weight of the sucrose fatty acid mono-ester.

The compressed tablet according to the invention may in addition to the granulate and the lactose further optionally includes up to 30 wt. % of other tablet excipients. These further tablet excipients are advantageously chosen from the group consisting of coloring agents, flavoring or taste masking agents, muco-adhesive agents, diluents, binders, lubricants, additional disintegrants other than lactose, stabilizers, surfactants, glidants, plasticizers, preservatives and sweeteners. These tablet excipients may be distributed throughout the tablet or they may be contained in, for instance, an external coating, such as an enteric coating.

Suitable muco-adhesive agents that can be added to the compressed tablets are chosen from the group consisting of carbomers, cellulose derivatives, plant lectin, dextrin, hypromellose, chitosan, polyethylene oxide, alginate and combinations thereof. In a preferred embodiment the compressed tablets comprise 0-3 wt. % of muco-adhesive agents.

The additional disintegrants are advantageously chosen from the group consisting of crospovidone, croscarmellose sodium, sodium starch glycolate, hydroxypropyl cellulose, polacrilin potassium, pregelatinized starch, microcrystalline cellulose and combinations thereof. In a preferred embodiment the compressed tablets comprise up to 20 wt. % of additional disintegrants.

The compressed tablets of the present invention may suitably comprise one or more coatings layers. These layers together represent no more than 20 wt. % of the tablet.

In order to enable easy removal of the compressed tablets from the moulds, the compressed tablets typically contains 0.1-10 wt. % of a lubricant or gliding agent. Preferably, the lubricant or gliding agent is selected from the group consisting of talc, sodium stearyl fumarate, magnesium stearate, calcium stearate, hydrogenated castor oil, hydrogenated soybean oil, polyethylene glycol, starches, anhydrous colloidal silica and combinations thereof. In a preferred embodiment the compressed tablets comprise 0.5-2 wt. % of lubricant.

According to a preferred embodiment, the compressed tablets of the present invention comprise a combination of silica and lubricant.

Advantageously, the compressed tablets exhibit a certain level of porosity in order to allow easy water access. Typically, the compressed tablets of the present invention exhibit a porosity of 1-50%, preferably of 2-15%, said porosity being defined as the volume of void space in the compressed tablets divided by the total volume of the compressed tablets, multiplied by 100. Analysis techniques for determining porosity of solid pharmaceutical dosage forms are known to those skilled in the art.

Another aspect of the invention relates to a method of manufacturing a compressed tablet as described herein before, said method comprising the steps of:

providing a lactose powder having a mass weighted average diameter of 32-250 μm, preferably of 45-250 μm;

combining the lactose powder with a granulation fluid to produce a granulate, said granulation fluid comprising a solution of CBD, sucrose fatty acid mono-ester and optionally further granulate excipients in an organic solvent;

removing the organic solvent by evaporation to obtain the granulate;

mixing the granulate with lactose and optionally further tablet excipients to produce a tablet mixture; and compressing the tablet mixture into a tablet.

In accordance with a preferred embodiment of the present method, the granulation fluid is combined with the lactose powder by gradually adding the granulation fluid to the lactose powder, whilst agitating the lactose powder. The granulation fluid may suitably be added onto a powder bed which is agitated under the influence of an impeller (e.g. in a high shear granulator, screws (e.g. in a twin screw granulator) or air (e.g. in a fluidized bed granulator). More preferably, the granulate is produced in a high shear granulator.

As is known to those skilled in the art, the rate of adding the granulation fluid to the powder, the ratio of granulation fluid to powder and the degree of agitation of the wet mass all affect the final particle size distribution of the granules. It is within the skills of the expert in the field of pharmaceutical drug formulation to steer at the desired particle size distribution.

Preferably, the amount of granulation fluid employed in the preparation of the granulate is in the range of 5-100% by weight of the lactose powder with which it is combined. Even more preferably, granulation fluid is employed in an amount of 10-50%, most preferably of 20-25% by weight of said lactose powder.

The granulation fluid is typically combined with the lactose powder at a rate of at least 3 ml per kg of lactose powder per minute. Even more preferably the addition rate is in the range of 4-250 ml/kg/min, most preferably in the range of 5-150 ml/kg/min.

In a preferred embodiment, the temperature of the granulation fluid is between 15° C. and 50° C. when it is combined with the lactose powder.

The organic solvent contained in the granulation fluid is preferably $C_1$-$C_3$ alcohol, more preferably a $C_1$-$C_3$ alcohol chosen from the group consisting of methanol, ethanol, n-propanol, isopropyl alcohol and combinations thereof. In a particularly preferred embodiment, the $C_1$-$C_3$ alcohol is ethanol.

Evaporation of the organic solvent can be accomplished by any means known in the art. In a preferred embodiment, vacuum drying is applied to remove the organic solvent. In a more preferred embodiment, the vacuum drying is applied at a temperature of between 20° C. and 70° C., even more preferably at a temperature of between 35° C. and 55° C.

In another preferred embodiment, the granulation fluid is prepared by combining the CBD, sugar fatty acid mono ester and optionally further granulate excipients, in the (relative) amounts recited here above, in an organic solvent at a combined total level within the range of 0.3-1.9 g per ml of solvent, more preferably within the range of 0.5-1.5 g per ml of solvent, most preferably within the range of 0.7-1.4 g per ml of solvent.

In a preferred embodiment of the invention, the granulation fluid comprises a dispersion or solution in the organic solvent of:

0.1-0.5 g/ml of CBD;
0.2-1 g/ml of sugar fatty acid mono-ester; and
0-0.4 g/ml of other granulate excipients;

preferably at a combined total level within the range of 0.3-1.9 g per ml of solvent, more preferably within the range of 0.5-1.5 g per ml of solvent, most preferably within the range of 0.7-1.4 g per ml of solvent.

In a preferred embodiment of the invention, the ratio of CBD to sucrose fatty acid mono-ester (w/w) in the granulation fluid is within the range of 1:4-1:1, more preferably 1:3-1:1.5.

The compressed tablets of the present inventions are conveniently produced in a tabletting machine. Tablet manufacturing methods by powder compression are generally known to those skilled in the art.

Another aspect of the invention relates to compressed tablets comprising CBD as defined herein for use in the treatment of psychosis disorders or anxiety disorders, said treatment comprising peroral administration of one or more the compressed tablets in an amount that is equivalent to 10-200 mg of CBD.

CBD-containing compressed tablets according to the invention are particularly suitable for use in the treatment of a psychosis disorder selected from schizophrenia, schizophreniform disorder, schizoaffective disorder, brief psychotic disorder, delusional disorder, shared psychotic disorder, paraphenia. According to a particularly preferred embodiment, the tablets are used in the treatment of a psychosis disorder selected from schizophrenia, schizophreniform disorder, schizoaffective disorder, paraphenia.

According to another preferred embodiment, the compressed tablets according to the present invention are used in the treatment of an anxiety disorder selected from phobic disorder, generalized anxiety disorder, post-traumatic stress disorder, panic disorder, obsessive-compulsive disorder, agoraphobia. According to a particularly preferred embodiment, the tablets are used in the treatment of an anxiety disorder selected from phobic disorder, generalized anxiety disorder, post-traumatic stress disorder.

In a preferred embodiment said treatment comprises peroral administration of one or more of the compressed tablets in an amount that is equivalent to 5-1000 mg of CBD, even more preferably in an amount that is equivalent to 10-750 mg and most preferably in an amount that is equivalent to 15-500 mg of CBD.

According to another preferred embodiment, the treatment comprises peroral administration of the compressed tablets in a daily amount that is equivalent to 5-1000 mg of CBD, even more preferably in a daily amount that is equivalent to 15-500 mg of CBD In another preferred embodiment, said treatment comprises peroral administration of 1 to 10 compressed tablets per day, more preferably 1 to 5, even more preferably 1 to 3 tablets per day. The tablets are conveniently administered at regular time intervals in the range of 4-24 hours, such as one tablet every 4 hours, every 6 hours, every 8 hours, or once a day.

Treatment of psychosis disorders or anxiety disorders in the context of the present invention involves both therapeutic and prophylactic treatments.

The compressed tablets of the present invention are advantageously employed in the treatments of mammals, preferably of humans.

The following examples are meant to further illustrate the invention and some of its preferred embodiments without intending to limit its scope.

EXAMPLES

Example 1

A CBD-containing granulate was prepared via a wet-granulation method. The composition of the CBD-granulate is described in Table 1.

TABLE 1 composition of CBD-granulate

| Component | wt. % |
|---|---|
| CBD | 8.0 |
| Sucrose mnonolaurate | 16.0 |
| Ascorbic acid | 0.8 |
| Lactose[1] | 75.2 |

[1] spray-dried α-lactose monohydrate, direct compression grade, mass weighted average diameter appr. 150 μm A granulation fluid containing CBD, sucrose monolaurate (SML) and ascorbic acid (AA) at a combined concentration of 1.2 g/ml was prepared as follows. The required amount of CBD was weighed in a beaker. In another beaker, the AA was dissolved in 165 ml of ethanol. The solution was heated to 60° C. and stirred to help the dissolution of AA. Dissolution of AA was completed in approximately 15 minutes. When the AA had been dissolved, this solution was added to the beaker containing the CBD. The required amount of SML was also added to the beaker containing the CBD. The mixture was heated to 45° C. and stirred to help the dissolution. This granulation fluid was stirred during 10 to 15 minutes until all the material had been dissolved.

The wet granulation process was performed as follows. Lactose was weighed and transferred to the mixing bowl of a high shear granulator. The system was closed and the heating for the heating jacket of the granulation vessel was turned on (set temperature of 40° C.). Before addition of the granulating fluid, vacuum was applied and nitrogen was pumped into the vessel. Subsequently, the granulating fluid was added by dripping using a peristaltic pump with a flow of 9 ml/min while the impeller and the chopper were turning. When the granulating fluid was completely added to the granulation vessel, the drying process started. Vacuum drying occurred under a stream of nitrogen (200 ml/min). The drying process was completed when the temperature (50° C.) and vacuum remained stable for at least 15 minutes and no liquid was coming from the condenser.

After completion of the drying process, the vacuum was released, the nitrogen flow was closed and the granulate was collected and transferred to a sieve. The granulate was sieved through sieves of 2.0 mm, 0.710 mm and 0.355 mm. The final granulate was packed into an aluminum bag. The CBD-granulate had a mass weighted average diameter of 355 μm. The binding component of the granulate consisted of a solid dispersion of CBD in SML.

Example 2

The CBD-granulate obtained in Example 1 was blended with excipients and directly compressed into tablets for peroral administration. The components used for tablet preparation are given in Table 2. A specification of the compressed tablets is given in Table 3.

TABLE 2 composition used for the preparation of a 340 mg tablet comprising ~20 mg CBD

| Component | wt. % |
|---|---|
| Granulate | 75 |
| Lactose[1] | 23.8 |
| Magnesium stearate | 1 |
| Silicon dioxide, anhydrous | 0.2 |

[1] spray-dried α-lactose monohydrate, direct compression grade, mass weighted average diameter appr. 150 μm

TABLE 3 specification of the compressed tablets

| Parameter | Method | Specification |
|---|---|---|
| Hardness | Ph. Eur. 2.9.8 | ≥20 N |
| Diameter | — | 10 mm |
| THC content | HPLC | ≤0.5% |
| Dissolution | Ph. Eur. 2.9.3 | ≥75% (Q) within 45 minutes |
| Disintegration | Ph. Eur. 2.9.1 | <15 minutes |
| Residual ethanol | Ph Eurr. 2.4.24 | ≤5000 ppm |

Example 3

The rate of dissolution of CBD from the compressed tablets described in Example 2 was tested according to European Pharmacopeia (Ph. Eur. 2.9.3) for oral tablets. The rate of dissolution of pure CBD (20 mg) was determined using the same method.

The dissolution medium consisted of a solution of 1 wt. % SDS in water. The pH of the medium had been adjusted to 7 with diluted HCl. During the experiments, the temperature of the dissolution media was maintained between 36 and 41° C. under stirring. After dropping the tablet in the dissolution medium, samples were taken at various time intervals with a disposable syringe. The samples were filtered immediately over a syringe filter into a HPLC vial and analyzed by HPLC. The results of the dissolution tests are summarized in Table 4

TABLE 4

| | % (w/w) of THC dissolved | |
|---|---|---|
| Time (in min.) | Tablet | CBD pure |
| 1 | 2.8 | 2.6 |
| 4 | 21.5 | 9.2 |
| 8 | 45.0 | 18.6 |
| 15 | 65.4 | 27.4 |
| 30 | 70.3 | 35.2 |
| 45 | 69.1 | 42.4 |
| 60 | 74.2 | 45.5 |

Example 4

Tablets from example 2 were packaged in aluminum pouches. These packaged tablets were stored under different storage conditions of 20° C.±5° C. and 40° C. for 1 year. The tablets were found to be stable under these storage conditions, i.e. CBD content after storage was still more than 90% the original content.

Example 5

This example describes the production of a CBD-granulate in a Rotavapor. The composition of the granulate is described in table 5.

TABLE 5

| Component | wt. % |
|---|---|
| CBD | 6.7 |
| Sucrose monolaurate | 13.3 |
| Ascorbic acid | 0.7 |
| Lactose [1] | 79.4 |

[1] spray-dried α-lactose monohydrate, direct compression grade, mass weighted average diameter appr. 150 μm The granulation fluid was preparing dissolving the ascorbic acid (1.3 g) in 50 ml of ethanol and heating at 60° C. When the ascorbic acid was dissolved the corresponding amount of sucrose monolaurate (26.6 g) and CBD (13.3 g) were added and the solution was stirred until all the material was dissolved.

The lactose (58.8 g) was introduced in a round bottom drying flask and part of the granulation fluid was carefully poured on the lactose. The material was mixed and dried at 40° C. The rest of the granulation fluid was added and the mixing and drying was repeated until total solvent evaporation.

Subsequently, additional lactose (100 g) and ethanol (appr. 60 g) were added and drying was continued at a temperature of 60° C. The final granulate was sieved through a 0.355 mm sieve.

Example 6

The CBD-granulate obtained in Example 5 was blended with excipients and directly compressed into tablets comprising 10 mg CBD for peroral administration. The compressed tablets had an average weight of 200 mg and were composed of 75 wt. % of the CBD-granulate, 23.8 wt. % of spray-dried α-lactose monohydrate, 1% of magnesium stearate and 0.2% of syloid. The tablets were packaged in aluminum pouches.

These tablets were submitted to a stability study during 1 year at −20° C., room temperature and 40° C., respectively. Tablets were found to be stable under all these storage conditions, i.e CBD content had decreased by not more than 10% during the storage period.

Example 7

A CBD-granulate was produced as explained in example 1 but using as excipient a mixture of 75 wt. % lactose and 25% microcrystalline cellulose. Compressed tablets were produced in the same way as described in Example 2 and packaged in aluminum pouches.

These tablets were subjected to a stability study by keeping them for 6 months at room temperature. The tablets described in Example 2 were subjected to the same stability test.

After 6 months the CBD content of both types of tablets had decreased by not more than 10%. After the 6 months of storage the level of impurities found in the tablets produced with the blend of lactose and microcrystalline cellulose was twice as high as in the tablets of Example 2.

Example 8

Oral tablets containing 11 mg CBD as described in example 6 and a soft-gel capsule containing 200 mg of pure CBD (powder) were used in a pharmacokinetic study. Following ingestion of the capsule or 18 of the aforementioned tablets by a healthy volunteer, resulting in a dose of 200 mg CBD in both cases, plasma concentrations of CBD were analyzed using LC/MS/MS.

Peak plasma concentration ($C_{max}$), time to peak plasma concentration ($t_{max}$) and area under the curve from t=0 to infinity ($AUC_{(0,\infty)}$) were calculated. The results are summarized in Table 6.

TABLE 6

| Pharmacokinetic parameters | Capsule | Tablets |
|---|---|---|
| $C_{max}$ (ng ml$^{-1}$) | 2.0 | 112.7 |
| $t_{max}$ (min) | 150 | 120 |
| $AUC_{(0,\infty)}$ (ng ml$^{-1}$ min) | 1.2 | 121.2 |

The invention claimed is:

1. A compressed tablet having a tablet weight of 60-1200 mg and comprising:
   (a) 50-95 wt. % of a granulate;
   (b) 5-50 wt. % of lactose; and
   (c) 0-30 wt. % of other tablet excipients;
   wherein the granulate comprises:
   (i) 2-15 wt. % of cannabidiol;
   (ii) 2-30 wt. % of sucrose fatty acid mono-ester;
   (iii) 30-96 wt. % of lactose; and
   (iv) 0-25 wt. % of other granulate excipients,
   wherein the granulate is composed of granules comprising lactose particles that are held together by a solid dispersion comprising cannabidiol and sucrose fatty acid mono-ester and optionally other granulate excipients; and
   wherein the compressed tablet is obtained by:
   (a) providing a lactose powder;
   (b) combining the lactose powder with a granulation fluid comprising a solution of cannabidiol, sucrose fatty acid mono-ester and optionally other granulate excipients in an organic solvent;
   (c) removing the organic solvent by evaporation to produce a granulate;
   (d) mixing the granulate with lactose and optionally other tablet excipients to produce a tablet mixture; and
   (e) compressing the tablet mixture into a tablet.

2. The compressed tablet according to claim 1, wherein the tablet comprises 2-100 mg cannabidiol.

3. The compressed tablet according to claim 1, wherein the granulate is composed of granules comprising lactose particles that are held together by a solid dispersion comprising cannabidiol, antioxidant and sucrose fatty acid mono-ester and optionally other granulate excipients.

4. The compressed tablet according to claim 3, wherein the granulate is composed of granules comprising lactose particles that are held together by a solid dispersion, wherein the solid dispersion contains a dispersed phase comprising cannabidiol, said dispersed phase having a volume weighted average diameter between 2 nm and 1 μm.

5. The compressed tablet according to claim 1, wherein the lactose is anhydrous lactose or lactose monohydrate.

6. The compressed tablet according to claim 1, wherein granules comprised in the granulate have a mass weighted average diameter of 50-1000 μm.

7. The compressed tablet according to claim 1, wherein the granulate comprises 0.2-1.5 wt. % of antioxidant.

8. The compressed tablet according to claim 1, wherein the sucrose fatty acid mono-ester comprises saturated $C_{10}$-$C_{18}$ fatty acids.

9. The compressed tablet according to claim 1, comprising 0-5% of Δ9-tetrahydrocannabinol by weight of cannabidiol.

10. The compressed tablet according to claim 1, wherein the lactose powder has a mass weighted average diameter of 32-250 μm.

11. The compressed tablet according to claim 1, wherein the granulation fluid comprises an anti-oxidant.

12. A method of treating psychosis disorders or anxiety disorders, comprising perorally administering one or more compressed tablets according to claim 1 in an amount that is equivalent to 5-1000 mg of cannabidiol.

13. The method according to claim 12, wherein the psychosis disorder is selected from schizophrenia, schizophreniform disorder, schizoaffective disorder, and/or paraphenia.

14. The method according to claim 12, wherein the anxiety disorder is selected from phobic disorder, generalized anxiety disorder, and/or post-traumatic stress disorder.

* * * * *